United States Patent [19]

Miles et al.

[11] Patent Number: 5,757,484
[45] Date of Patent: May 26, 1998

[54] STANDOFF LASER INDUCED-BREAKDOWN SPECTROSCOPY PENETROMETER SYSTEM

[75] Inventors: Brian Herndon Miles, Tucson, Ariz.; Stafford S. Cooper; Ernesto R. Cespedes, both of Vicksburg, Miss.; Greg A. Theriault, Encinitas, Calif.

[73] Assignee: The United States of America as represented by the Secretary of the Army, Washington, D.C.

[21] Appl. No.: 401,601

[22] Filed: Mar. 9, 1995

[51] Int. Cl.$^6$ ................................. G01N 21/63
[52] U.S. Cl. ................................. 356/318
[58] Field of Search ................... 356/317, 318, 356/72

[56] References Cited

U.S. PATENT DOCUMENTS

| | | | |
|---|---|---|---|
| 5,128,882 | 7/1992 | Cooper et al. | 364/550 |
| 5,316,950 | 5/1994 | Apitz et al. | 436/28 |
| 5,379,103 | 1/1995 | Zigler | 356/318 |

Primary Examiner—F. L. Evans
Attorney, Agent, or Firm—Luther A. Marsh

[57] ABSTRACT

The present invention describes a subsurface soil contaminant identification system method using a cone penetrometer unit for in-situ elemental composition identification in the form of solids, liquids or gasses. Elemental identification is achieved by using atomic spectral analysis of the contaminants that are stimulated by a laser induced breakdown of the soil contaminants to be determined. The system includes a high resolution spectrometer with array detector, a controller for control/data acquisition, a penetrometer push operation controller and data gathering equipment, an optical fiber link to a cone penetrometer with improved optical focusing components. The improved method of using the system entails: i) soil characterization during an initial penetrometer push, then ii) contaminant identification during the penetrometer retrieval phase from a soil bore hole formed during the initial push. The LIBS based system and method is applicable to elemental atomic detection, identification and concentration quantification of soil contaminants. The method can simultaneously detect several metals during a one data sampling.

15 Claims, 4 Drawing Sheets

STANDOFF LASER INDUCED-BREAKDOWN SPECTROSCOPY PENETROMETER SYSTEM

STATEMENT OF GOVERNMENT INTEREST

The invention described herein may be manufactured and used by or for the Government of the United States of America for governmental purposes without the payment of any royalties thereon.

FIELD OF THE INVENTION

This invention pertains to the determination of subsurface soil and water borne contaminants and hazardous wastes. In particular, the invention pertains to in-situ identification of elemental composition of the subsurface soil and entrained contaminant species by use of spectral signatures thereof by laser induced-breakdown spectrosacopy.

BACKGROUND OF THE INVENTION

Environmental concern of soil and groundwater contamination along with governmental mandated requirements to remedy this problem has prompted the need for rapid and cost effective subsurface characterization methods of the chemical contaminants therein. Of these contaminants, a grouping known as heavy metals is of great concern since they are prevalent in most contaminated waste sites and are toxic to humans.

Prior traditional subsurface soil characterization techniques for these purposes include collection of field samples and subsequent analysis in the laboratory for both chemical and elemental analysis. The samples are initially collected by a bore hole or penetrometer sampler which in turn is taken to a lab where subsequent standard analysis techniques such as atomic absorption or inductively coupled plasma emission processes determine contaminants and concentration thereof in the soil. These traditional techniques relatively long time periods from sample extraction and preparation to laboratory analysis thereof. This is not a suitable technique for examining large land areas where soil contamination has occurred. Additionally, these earlier techniques are prone to error due to loss of soil sample material prior to laboratory analysis, thus less accurate analytical results occur.

Another more recent technique suitable for elemental metal determination in soil is anodic stripping voltametry. This method uses a metal anode which is initially charged for attracting metal-ions in a sample. Next, the condition of anode charging is cut off allowing the different metal-ions to separate from the electrode at different delay times. This technique is only suitable for liquid-phase based soil analysis since it relies on metal-ion migration in an aqueous solution, thus groundwater must be present in a borehole under examination for this technique to be effective. Furthermore, delay times during a single location analysis is on the order of 5-15 minutes which results in an expensive testing procedure due to substantial time periods required for each penetrometer push. In the instant invention's method, groundwater does not have to be present.

Other current techniques for both elemental and molecular material determination that use use real-time, remote, in-situ monitoring techniques using a cone penetrometer unit are: i) fluorescent spectroscopic based systems and ii) laser-induced breakdown spectroscopic (LIBS) based systems that use emission spectra of elemental materials. Both fluorescent and LIBS systems are effective techniques for different materials to be determined by irradiating the soil sample at different radiant intensities. A fluorescent based technique is primarily used for examination of molecular materials such as petroleum hydrocarbons since fluorescent activity occurs when excited. The LIBS technique is primarily used for determining elemental atomic contaminants such as metals by breaking down molecular bonds of soil materials and reducing molecules into component atomic species which are in a plasma state that in turn produce emission spectrum of the atomic species. In system form, these two techniques use different light excitation sources and components for focusing the light due to the differing required power levels for determining particular materials.

A fluorescent based soil contamination determination technique is taught in U.S. Pat. No. 5,128,882 of Cooper et al. entitled "Device for Measuring Reflectance and Fluorescence of In-Situ Soil" and U.S. Pat. No. 5,316,950 of Apitz et al. entitled "Method for Quantitative Calibration of In-Situ Optical Chemical Measurements in Soils Using Soil Class and Characteristics." Both of these teachings use a real-time, in-situ penetrometer probe that use either a light source or low powered laser source, e.g. an $N_2$ laser. These light sources use low light power levels in the $10^4$ W/cm$^2$ range or less. These teachings are concerned determining what kinds of molecular type chemical contaminant are present in the soil, e.g. petroleum hydrocarbons using their fluorescent spectra when excited by the electromagnetic light source.

In contrast, the LIBS based system requires much higher irradiance values in the $10^8$ W/cm$^2$ power range for proper excitation of metallic materials for their respective emission spectra. The LIBS based system requires features not found in a fluorescent based system such as a more durable light focusing subsystem for transmitting and receiving light signals in such a system due to the high peak irradiance values used. In particular, dielectric breakdown of a soil contaminant material requires flux values approximately 3 to 4 orders of magnitude greater than those needed for a fluorescent based system. Indeed, LIBS is not a soil contamination determination system for use in quantifying molecular specie concentrations since most molecular materials in the soil dissociates during plasma production. An example of the LIBS based system is taught in U.S. patent application Ser. No. 08/074,575 by Ballard et al. entitled "Laser Induced Breakdown Spectroscopy for Detection of Heavy Metal Soil Contaminants" which is assigned to the U.S. Government and also hereby incorporated by reference. This disclosure teaches of the LIBS based system that includes appropriate spectroscopy data acquisition equipment, a high energy laser source, e.g., Nd:JAG or excimer laser source, an optical fiber link connected thereto and appropriate lens focusing components in a cone penetrometer unit.

Accordingly, the present invention is an improvement of an in-situ soil contaminant LIBS based system that provides a more reliable and robust cone penetrometer unit with an improved method for the use thereof.

SUMMARY OF THE INVENTION

The present invention describes a subsurface soil contaminant identification system method using a cone penetrometer unit for in-situ elemental composition identification in the form of solids, liquids or gasses. Elemental identification is achieved by using atomic spectral analysis of the contaminants that are stimulated by a laser induced breakdown of the soil contaminants to be determined. The system includes a high resolution spectrometer with array detector, a controller for control/data acquisition, a penetrometer push operation controller and data gathering equipment, an optical fiber link to a cone penetrometer with improved optical focusing components. The improved method of using the system entails: i) soil characterization during an initial penetrometer push, then ii) contaminant identification during the penetrometer retrieval phase from a soil bore hole formed during the initial push. The LIBS based system and method is applicable to elemental atomic detection, identification and concentration quantification of soil contaminants. The method can simultaneously detect several metals during a one data sampling.

OBJECTS OF THE INVENTION

Accordingly, several objects of the present invention are:

(a) To provide a LIBS based soil contaminant determination system with a more reliable and cost effective system.

(b) To provide a LIBS based soil contaminant system with a method can collect geophysical data during an initial penetrometer push and then a subsequent contaminant determination as the penetrometer is withdrawn from a soil bore hole.

(c) To provide a LIBS based soil contaminant system with an improved cone penetrometer unit with a stand-off optical focusing component for minimizing the deterioration thereof.

Still further advantages will become apparent from consideration of the ensuing detailed description.

DETAILED DESCRIPTION

The penetrometer operation and data acquisition is similar to that discussed in U.S. patent application Ser. No. 08/074, 575, except for the optical components in the penetrometer unit and the method of using the LIBS based system. The penetrometer unit in the instant invention can be used in with the LIBS based system disclosed in earlier U.S. patent application Ser. No. 08/074,575 where adverse soil conditions are encountered and higher power levels of irradiance may be required.

The invention herein provides a durable and reliable penetrometer unit where the separation distance between the soil under examination and the optical focusing/receiving components in the penetrometer unit is maximized. This separation distance is critical since: (i) optical components such as windows and lenses in the optical path as disclosed in the earlier U.S. patent application Ser. No. 08/074,575 can rupture and pit by: a) the high radiant energy used for laser induced breakdown of the soil and b) the resulting generated hot plasma and shock wave of the soil; by positioning the penetrometer's optical focusing/receiving components away from the focal point of induced breakdown, minimal damage is incurred thereto; (ii) reliable data measurements requires that unobstructed light transmissions occur at the bore hole soil location under test where laser induced breakdown occurs, by recessing the optical focusing/receiving components location to an inward location towards the axis of penetrometer unit, less contamination to the optical focusing/receiving components occurs by strain relieved soil in the bore hole that is "flicked" off the edge of the penetrometer unit as the penetrometer unit is retrieved from the bore hole; and (iii) the penetrometer integrity an reliability is improved by not having to bend an optical fiber link within the penetrometer unit which often leads to optical fiber breakdown and destruction due to the high radiant power levels used. Moreover, the instant invention's co-axial optical focusing/receiving components within the penetrometer unit allows for flexibility as to the individual optical components used since only simple optical design constraints can be readily modified.

Figure 1:
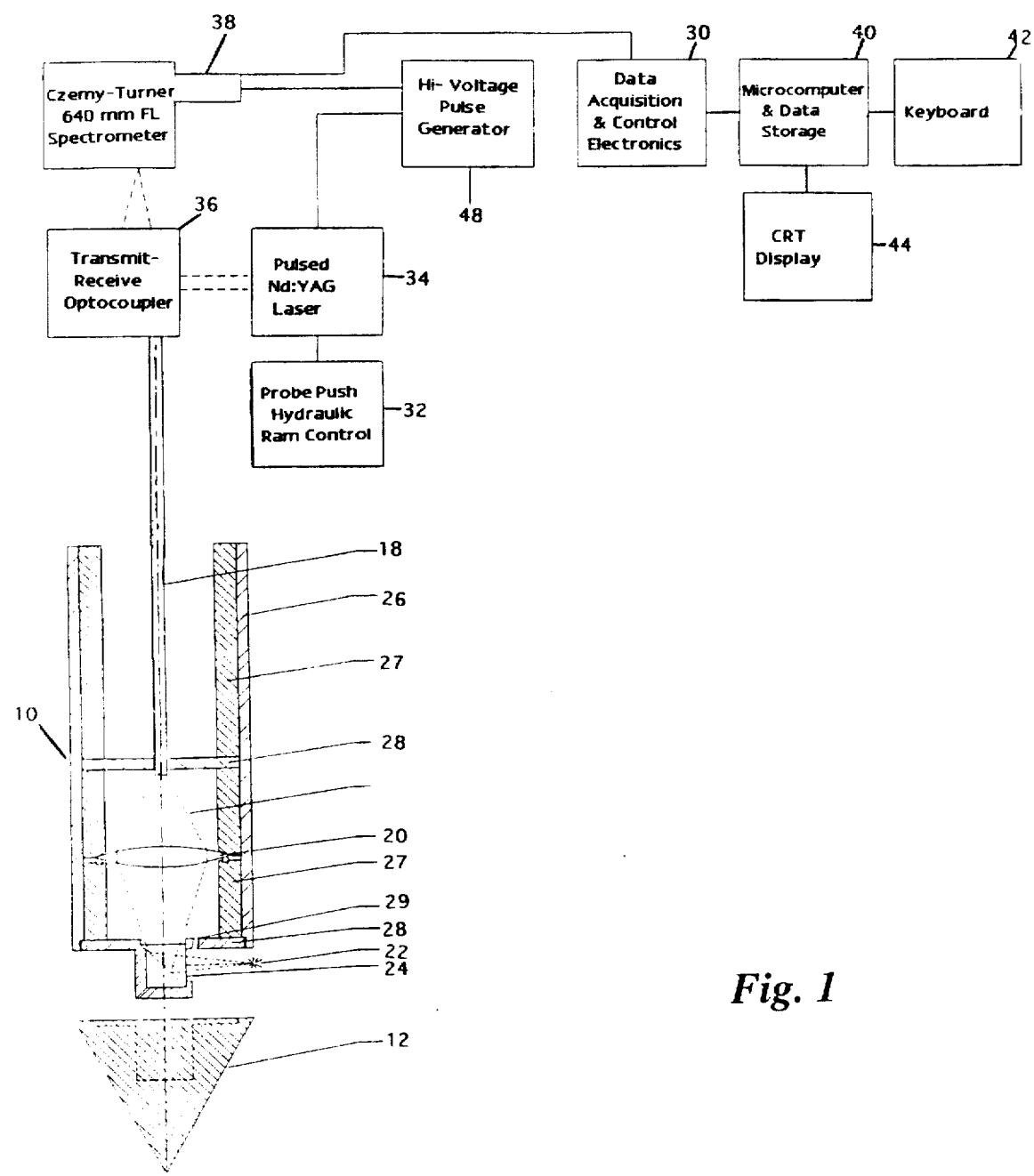
FIG. 1 illustrates a LIBS based system with a cone penetrometer with an improved optical focusing feature.
Figure 2:
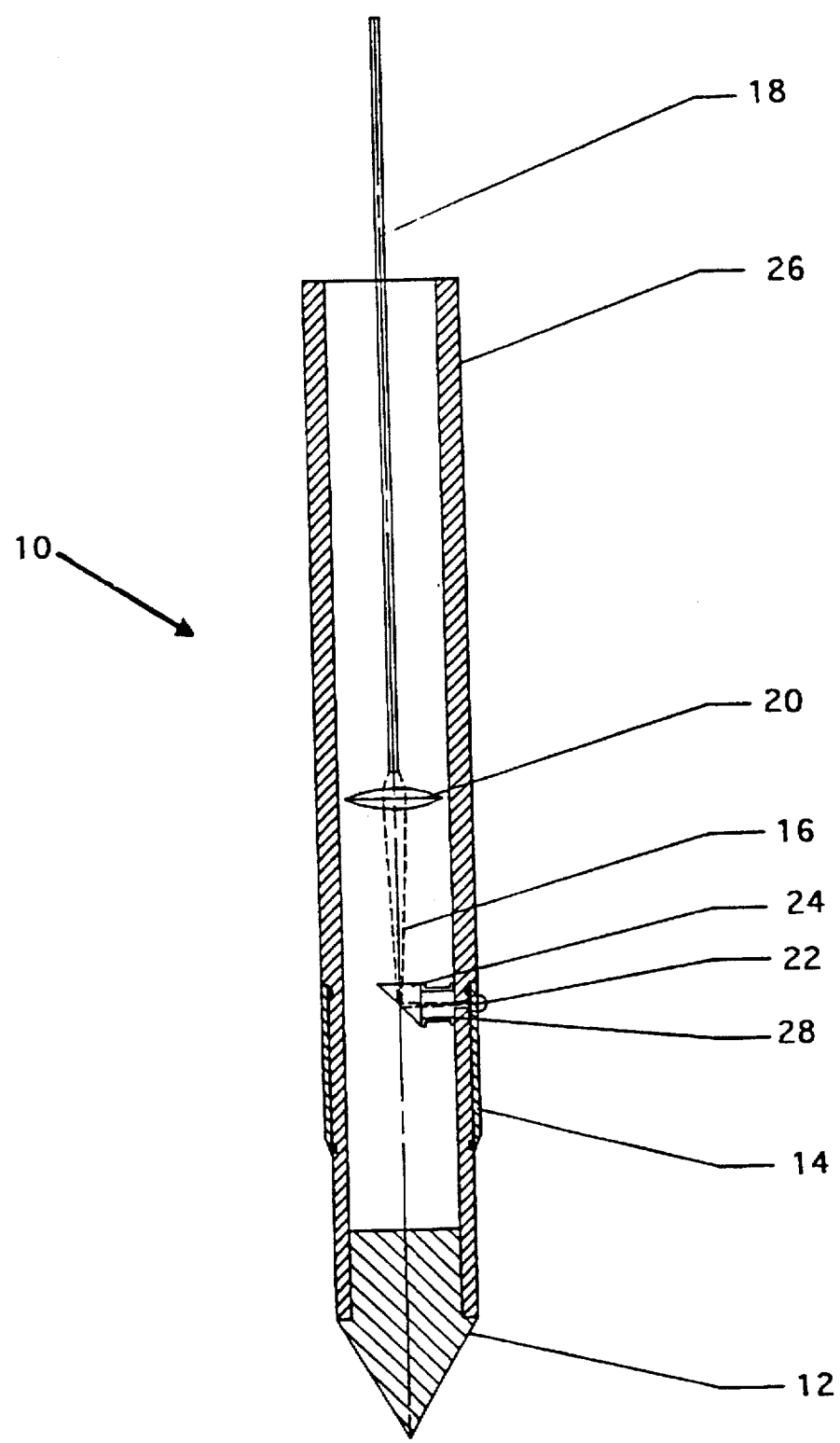
FIG. 2 illustrates another embodiment of the penetrometer with a sacrificial sleeve feature in cross-sectional view.

In operation, the penetrometer unit 10 in FIG. 1 pushes to a desired maximum soil depth. Before retraction of the unit 10, a cone tip 12 may be dropped. Alternatively, the unit 10 may drop a sacrificial sleeve 14 as shown in the design of FIG. 2. The penetrometer 10 is retrieved to the surface while making LIBS measurements by the exposed and recessed prism 24. In practice, this is an effective technique since a soil bore hole wall has been formed by the initial penetrometer push which forms an egress for the unit 10. The unit 10 can also include standard geophysical sensors such as tip resistance and sleeve friction stress sensors in the cone tip 12 that provides soil classification data, e.g. soil stratigraphical data, during an initial penetrometer push. Such soil classification techniques are well known in the art as taught in the above discussed U.S. Pat. No. 5,316,950 where strain gauge sensors are used for this purpose. The penetrometer unit 10 is usually a cylindrical unit made of a steel outer housing 26 with an upper internal support element 28 for support to the end of optical fiber 18 and lower support element 28 for support of the prism 24. The outer housing 26 has an upper and lower lens barrel 27 made of metal or plastic that provides structural support for prism 24 and a condensing lens 20 respectively. The lower prism support structure 28 includes a prism purge port 29 for maintaining uninterrupted optical transmissions through prism 24 during plasma generation of the soil. The penetrometer unit 10 may also use a high temperature heater coil element immediately above the reduced diameter section of the penetrometer unit 10 of FIG. 1 to reduce moisture prior to generating the plasma.

Light pulses are transmitted through optical fiber 18 through the condensing lens 20 over optical path 16, then through the prism 24 and focused at a focal point 22 where laser induced breakdown of the soil occurs, whereby the coherent electromagnetic radiation induces multiphoton ionization of the soil contaminants and a corresponding electromagnetic spectrum that is collected at an optical focusing port. A data acquisition and control electronics unit 30 is cued by the movement of the penetrometer unit 10 by a probe push hydraulic control unit 32. The hydraulic control unit is master in the control of the system when operating under normal data acquisition conditions when there is movement of unit 10. The method of using the system requires data collection during: i) the initial penetrometer push for soil classification determination and ii) then the penetrometer retrieval for determination of soil contaminants using LIBS technique. The automatic control of the system can be overridden to provide multiple test examinations of the same spot in a bore hole if required. The probe push hydraulic control unit 32 sends a logic signal to laser 34 indicating the push or withdrawal is being made and sends this signal at a rate proportional to the push or retrieval speed through a high voltage pulse generator unit 48 that acts as a shutter control of the detection array 38 on spectrometer unit 50 in conjunction with the data acquisition and control electronics unit 30 so as to spatially sample the soil in consistent intervals. The laser 34 is typically a Nd:YAG pulsed laser capable of pulse energies of at least 50 millijoules at 1064 nm. The laser 34 can also be an excimer laser source. After receiving the logic signal from probe push hydraulic control unit 32, laser 34 fires a light pulse into a transmit/receive opto-coupler 36 via an optical link which: i) directs laser light into the fiber 18 for transmit down the penetrometer unit 10 and ii) redirects a portion of the returned emission signal of the contaminants to the spectrometer analysis unit 50 which is preferably a Czerny-Turner 640 mm FL spectrometer unit with a gated 1024 element silicon linear diode array unit 38 attached. The optical fiber link 18 can be either a single or multiple optical fiber link for transmit and receive purposes where a multiple fiber configuration would be for dedicated optical channels as taught in U.S. patent application Ser. No. 08/074,575. The data acquisition and control unit 30 operates in conjunction with computer 40 with that includes a standard CRT display 42 and keyboard 44.

The pulse emerges from the fiber link 18 and is focused by the condensing lens 20, or alternatively by multiple lenses, onto the soil surface at the focal point 22 after first being redirected by the prism 24, or alternatively by a mirror/window optical combination. The light beam continues to narrow while passing through the prism 24 until it reaches the focal point 22 on the soil surface a few centimeters from the prism 24. The spot size of the focal point 22 is determined by the geometry of the designed penetrometer's optical components. A smaller spot size will produce more intense induced breakdown where a shorter lens to soil image distance occurs. When breakdown of the soil occurs, the plasma is formed at approximately the focal point 22. The elemental species, particularly metals within the plasma, undergo transitions and radiate characteristic spectral lines. The optical components within the penetrometer unit 10 collect a portion of the breakdown radiation and re-image the breakdown spark with characteristic spectral lines on the end of fiber surface 18 within the probe. Best spectral acquisition occurs hundreds of nanoseconds after the breakdown. In temporal terms, there is no interference in transmitted laser light and the re-imaged received spectral radiation. The other end of fiber 18 can be either: i) connected to the spectrometer unit 50 directly if there is no opto-coupler 36 and there is a dedicated receive fiber, or ii) a portion of the light is reflected off opto-coupler 36 and redirected to spectrometer unit 38 if fiber link 18 has dual use transmit/receive capability as shown in FIG. 1. The spectrometer 50 with a gated array detector unit 38 disperses the light into constituent optical wavelengths and converts the optical energy into an electronic signal to be transmitted to controller unit 30. The full spectrum of one observed epoch is recorded by the computer and data storage unit 40 which can be processed for elemental identification and concentration by use of well known spectroscopic analysis techniques using certain spectral peak(s) which corresponds to a specific element and peak intensity or peak area thereof which indicates the concentration of the material. Complete analysis of the spectral information produced by the LIBS based system herein may be provided by a comparison of the spectral information with standards prepared prepared by mixing known quantities of contaminants with soil similar to that found at the test site. Variations in specific spectral properties are measured and calibration cures are constructed which relate the concentration of a specific contaminants in soil to particular spectral characteristics. These methods are well known in the art and need not be described in detail. Thus, the LIBS based system determines the type, location, depth and quantity of contaminants at the test site.

Figure 3:
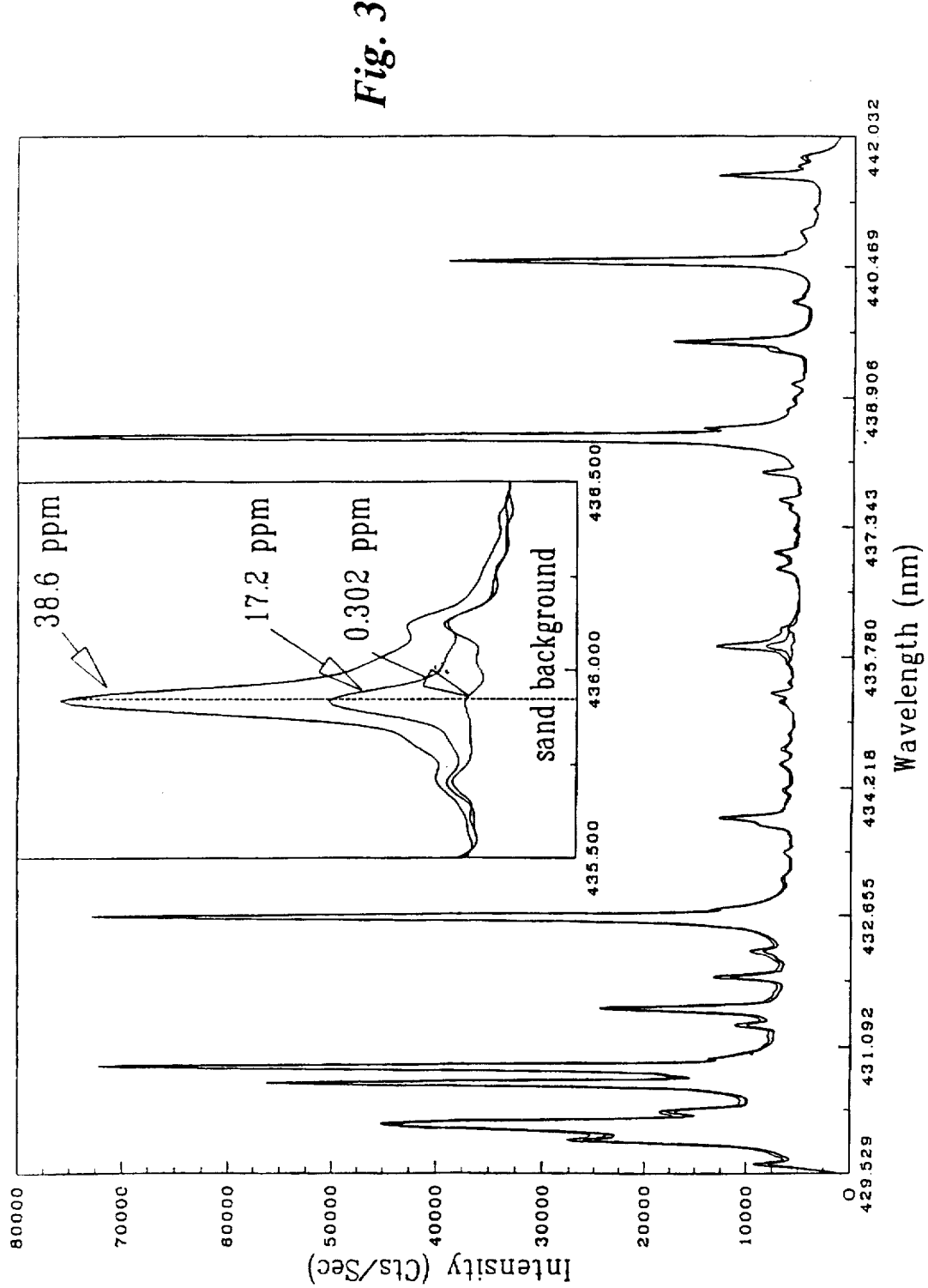
FIG. 3 shows spectra data results of three sand samples with mercury therein using the LIBS based system.
Figure 4:
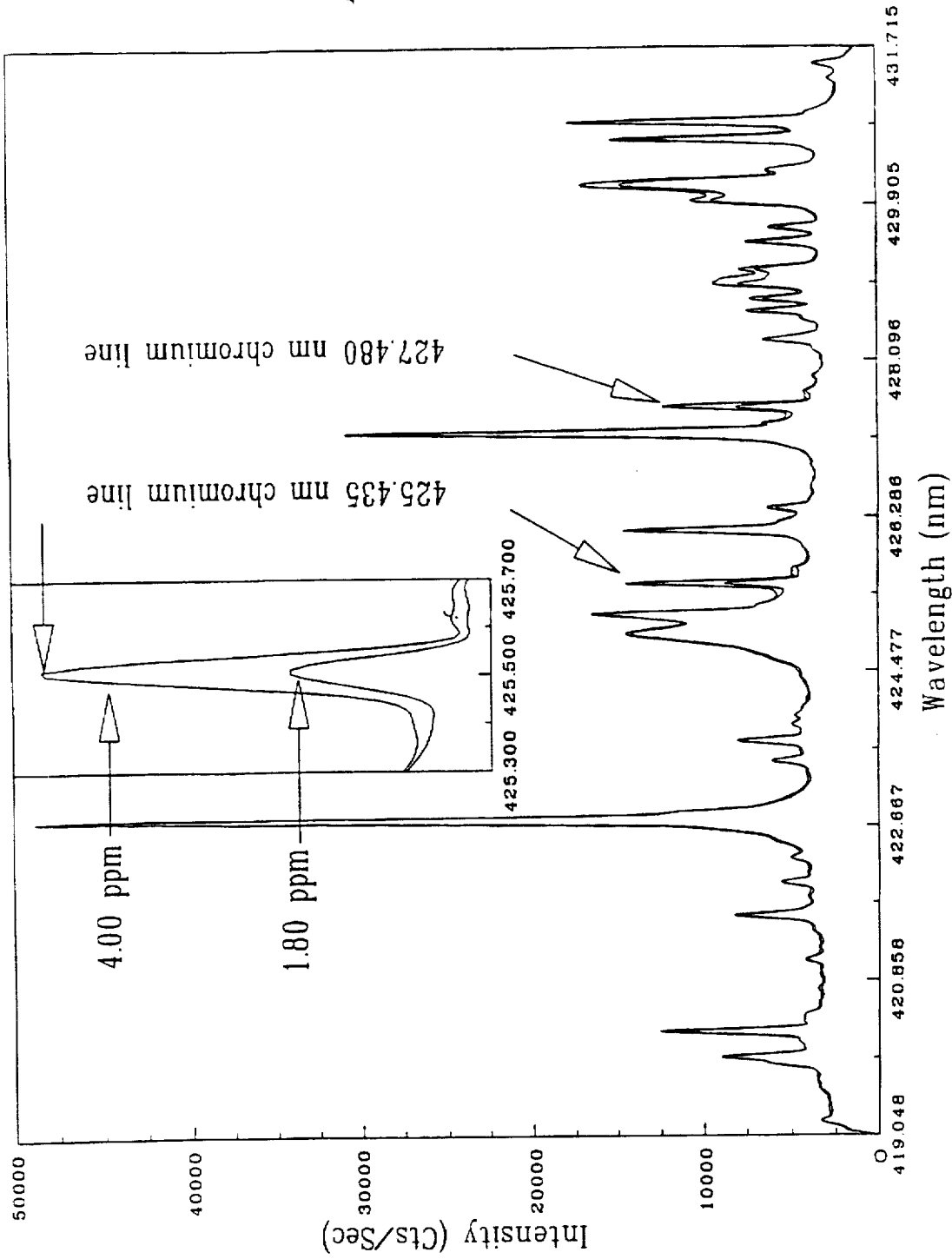
FIG. 4 shows spectra data results of three sand samples with chromium therein using the LIBS based system.

FIG. 3 illustrates test results using the LIBS based system where spectra of three sand samples containing 0.3 parts per million (ppm), 17.2 ppm, and 36.6 ppm of mercury respectively. The significant peak located at 435.835 nm corresponds to the mercury atomic line. FIG. 4 shows similar data for chromium in sand at concentrations of 1.8 ppm in sand, 4.00 ppm, and shows the dependence of peak intensity on metal concentration. The method provided herein can simultaneously detect several heavy metals in one epoch of data sampling.

Although the description above contains many specificities, these should not be construed as limiting the scope of this invention as set forth in the appended claims, but as merely providing illustration of the presently preferred embodiments of this invention.

We claim:

1. Apparatus for in-situ determination of soil contaminants comprising:

a penetrometer for penetrating the soil, the penetrometer having an inner hollow chamber, an outer soil contacting wall, an optical unit that includes an optical directing means for directing and transmitting electromagnetic (EM) radiation through an optical focusing port, the optical unit is structurally supported by the outer soil contacting wall, the optical focusing port is unobstructed by the outer soil contacting wall and is disposed within a smaller, coaxially aligned space of the outer soil contacting wall, and an optical transmission means coupled to the optical unit for transmitting optical measurements;

an EM source means for generating coherent EM radiation that is coupled to the optical transmission means which passes through the optical focusing port to irradiate a soil wall created by the outer soil contacting wall, whereby the coherent EM radiation induces multiphoton ionization of the soil contaminants and a corresponding EM spectrum that is collected at the optical focusing port; and a spectrum analyzer means for analyzing the corresponding EM spectrum that is collected at the optical focusing port, the analyzer means is optically coupled to the optical transmission means thereby producing a spectral signature for each locus of the soil through which the penetrometer passes, the spectral signatures containing information on the soil contaminants.

2. The apparatus of claim 1, wherein the penetrometer includes a pointed tip that facilitates penetration of the penetrometer into the soil and contains a strain gauge for stratigraphic measurements.

3. The apparatus of claim 2, wherein the pointed tip is detachable from the outer soil contacting wall that allows for unobstructed EM radiation transmissions and collections through the optical focusing port.

4. The apparatus of claim 2, wherein a detachable sleeve is part of the outer soil contacting wall thereby enabling unobstructed EM radiation transmissions and collections through the optical focusing port after an initial penetrometer push to a required soil depth and detachment of the detachable sleeve.

5. The apparatus of claim 1, wherein the optical unit is a prism.

6. The apparatus of claim 1, wherein the optical unit that includes the optical directing means for transmitting electromagnetic (EM) radiation through the optical focusing port is a mirror and lens respectively.

7. The apparatus of claim 1, wherein the optical transmission means within the inner hollow chamber includes an internal optical focusing means for focusing transmitted and collected EM radiation from the optical unit to an optical fiber link for enabling EM radiation transmissions to the spectrum analyzer means.

8. The apparatus of claim 1, wherein the EM source means is a laser light that produces pulses of EM energy sufficient to ionize the locus of soil under examination.

9. The apparatus of claim 1 furthering comprising a driving means for driving and controlling the penetrometer into the soil, the driving means also controls sampling rates of the penetrometer for effective data acquisition and a data storage and visual display means of the data produced by the spectrum analyzer means.

10. The apparatus of claim 1, wherein the spectrum analyzer means is a optical multi-channel analyzer.

11. The apparatus of claim 10, wherein the spectrum analyzer means further comprises means for comparing the spectral signature of the soil passing by the optical focusing port with predetermined spectral characteristics of similar soils having known quantities of contaminant admixed therewith.

12. A method for producing in-situ determination of soil contaminants comprising:
    pushing a soil penetrometer to a desired depth and collecting soil stratigraphical data;
    retrieving the soil penetrometer unit while irradiating a portion of the soil with a coherent electromagnetic (EM) energy source as the EM source passes through a bore formed in the soil for producing induced multiphoton ionization of the contaminants in the soil in the form of a spectral signature for each locus of the soil through which the penetrometer passes resulting from the irradiation of the soil;
    collecting the spectral signature data through an optical transmission means within the penetrometer and transmitting it to a spectrum analyzer means for analysis.

13. The method of claim 12, wherein prior to retrieval of the penetrometer, a recessed optical focusing port is exposed to a soil bore hole wall formed by the penetrometer during the pushing operation.

14. The method of claim 13, wherein the optical focusing port is exposed by detaching a detachable sleeve that is part of an outer wall of the penetrometer.

15. The method of claim 13, wherein the optical focusing port is exposed by dropping a detachable tip portion of the penetrometer.

* * * * *